United States Patent
Henning et al.

(10) Patent No.: US 11,338,121 B2
(45) Date of Patent: May 24, 2022

(54) MICRO-NEEDLE ARRAY COMPRISING A COLOR CHANGE INDICATOR

(71) Applicant: LTS LOHMANN THERAPIE-SYSTEME AG, Andernach (DE)

(72) Inventors: Andreas Henning, Koblenz (DE); Simone Marx, Koblenz (DE); Larissa Florin, Urbach (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 123 days.

(21) Appl. No.: 16/637,832

(22) PCT Filed: Aug. 13, 2018

(86) PCT No.: PCT/EP2018/071957
§ 371 (c)(1),
(2) Date: Feb. 10, 2020

(87) PCT Pub. No.: WO2019/030417
PCT Pub. Date: Feb. 14, 2019

(65) Prior Publication Data
US 2020/0171290 A1  Jun. 4, 2020

(30) Foreign Application Priority Data
Aug. 11, 2017  (DE) .................... 10 2017 118 419.8

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61M 2037/0023* (2013.01); *A61M 2037/0046* (2013.01); *A61M 2037/0053* (2013.01); *B81B 2201/055* (2013.01)

(58) Field of Classification Search
CPC ...... A61M 37/0015; A61M 2037/0023; A61M 2037/0046; A61M 2037/0053; A61M 2025/0008; A61M 2037/0061; A61M 2205/0244; A61K 9/0021; B81B 2201/055; A61B 2562/028; A61B 2562/12; A61B 5/685
See application file for complete search history.

(56) References Cited

U.S. PATENT DOCUMENTS

| | | | |
|---|---|---|---|
| 2007/0081977 A1 | 4/2007 | Horstmann | |
| 2010/0069726 A1* | 3/2010 | Levinson | G01N 33/54386 600/309 |
| 2010/0256064 A1 | 10/2010 | Woolfson et al. | |
| 2011/0224515 A1* | 9/2011 | Mir | A61B 5/150435 600/317 |
| 2012/0123341 A1 | 5/2012 | Birchall et al. | |
| 2014/0257188 A1* | 9/2014 | Kendall | A61M 37/0015 604/173 |
| 2018/0099133 A1 | 4/2018 | Heuser et al. | |

FOREIGN PATENT DOCUMENTS

| | | |
|---|---|---|
| DE | 10353629 A1 | 6/2005 |
| DE | 102014201605 A1 | 7/2015 |
| EP | 1281352 A1 | 2/2003 |
| WO | WO-2008091602 A2 | 7/2008 |
| WO | WO-2008150829 A1 | 12/2008 |
| WO | WO-2009081122 A1 | 7/2009 |
| WO | WO-2012153266 A2 | 11/2012 |
| WO | WO-2013053022 A1 | 4/2013 |
| WO | WO-2016162449 A1 | 10/2016 |

OTHER PUBLICATIONS

International Preliminary Examination Report for PCT/EP2018/071957 dated Nov. 29, 2019.
International Search Report for PCT/EP2018/071957 dated Apr. 2, 2019.
Written Opinion of the International Searching Authority for PCT/EP2018/071957 dated Apr. 2, 2019.
Pettit, H., "The incredible colour changing tattoos that monitor the blood sugar levels of people with diabetes in real-time", MailOnline, 2018, 6 pages.

* cited by examiner

*Primary Examiner* — Amber R Stiles
(74) *Attorney, Agent, or Firm* — Faegre Drinker Biddle & Reath LLP

(57) ABSTRACT

The invention relates to a microneedle array and to the use thereof for intradermal delivery, comprising a plurality of microneedles on a carrier, wherein this microneedle array is suitable for penetrating the skin of humans or animals and includes at least one color change indicator.

15 Claims, No Drawings

MICRO-NEEDLE ARRAY COMPRISING A COLOR CHANGE INDICATOR

CROSS-REFERENCE TO RELATED APPLICATIONS

This application is a national stage application (under 35 U.S.C. § 371) of PCT/EP2018/071957, filed Aug. 13, 2018, which claims benefit of German Application No. 10 2017 118419.8, filed Aug. 11, 2017, both of which are incorporated herein by reference in their entirety.

The invention relates to a microneedle array and to the use thereof for intradermal delivery, comprising a plurality of microneedles on a carrier, wherein this microneedle array is suitable for penetrating the skin of humans or animals and includes at least one color change indicator.

Microneedle systems and devices in which microneedle arrays are used for the painless intradermal (or transdermal) administration of substances, and in particular of medicinal drugs, are known from the prior art.

The skin consists of several layers. The outermost layer of the skin, this being the stratum corneum, has known barrier properties to prevent foreign substances from penetrating into the body and the body's own substances from exiting the body. The stratum corneum, which is a complex structure composed of compacted horny cell residues having a thickness of approximately 10 to 30 micrometers, forms a watertight membrane for this purpose to protect the body. This natural impermeability of the stratum corneum prevents most pharmaceutical agents and other substances from being administered through the skin as part of an intradermal delivery.

As a result, various substances are therefore administered, for example, by generating micropores or cuts in the stratum corneum and feeding or delivering a medicinal drug into or beneath the stratum corneum. In this way, it is also possible to administer a number of medicinal drugs subcutaneously or intradermally or intracutaneously, for example.

It remains difficult to establish in the prior art whether a microneedle array has sufficiently penetrated the skin, and the stratum corneum has been reached or this barrier has been overcome.

In the prior art, WO 2009/081122 A1 describes a monitoring system for the release of medicinal drugs via microneedles. However, the system is not capable of verifying a penetration into the stratum corneum since the included dye only provides information as to whether a substance, this being a medicinal drug here, has been released from the microneedles.

Furthermore, WO 2009/081122 A1 does not describes the use of suitable color change indicators, in particular pH indicators, in particular in the pH range between 4 and 8.

DE 10 2014 201 605 A1 describes the problem that sufficient skin penetration is not possible by means of a microneedle array and proposes for dyes to be present in microcapsules in a delivery system. However, the disadvantage is that such microcapsules require suitable pressure to burst open, and to allow the dye to emerge. The bursting of the microcapsules is consequently independent of the actual penetration of the skin and requires that a minimum pressure be exerted. The verification is thus indirect.

Such a dermal penetration indicator is subject to the general requirement that unambiguous visualization of a successful physical penetration into the stratum corneum or through the stratum corneum into the layers of the skin beneath (epidermis, dermis) has to take place, by means of the released penetration indicator.

The object is therefore to enable reliable verification of a sufficient penetration depth of the microneedles into the skin, and in particular into the stratum corneum, wherein a direct and immediate verification is possible.

The present invention, in particular, takes advantage of the fact that the pH value on the skin surface is 4 to 5.5 and, by comparison, the pH value of the stratum corneum is 6.5 to 7. Using a pH indicator, it is consequently possible to generate a visible color change during the passage from the skin surface into the stratum corneum. Moreover, a color change can also take place as a function of the surrounding area in the achieved penetration depth, and more particularly taking the intradermal surrounding area (SC, epidermis, dermis) into consideration, even without dependence on a pH value. This is especially helpful when this color change is accompanied by the penetration of microneedles into the skin.

According to the invention, such suitable substances are referred to as color change indicators. The term 'color change' means that a shift in the color takes place, including from colorless to not colorless, which is visible to the naked eye, preferably on the skin surface.

The invention thus relates to such a teaching having the features of claim 1, this being a microneedle array for use with intradermal delivery, comprising a plurality of microneedles on a carrier, wherein the microneedles include at least one color change indicator. A color change, in particular of a pH indicator, particularly advantageously indicates a sufficient penetration depth into the stratum corneum.

In another embodiment, the color change indicator can be present in the microneedles and in the carrier.

The microneedle array can comprise a plurality of microneedles so as to be able to release a substance via the skin or into the skin of a patient, wherein the microneedle array is placed onto the skin of the patient. Each of the microneedles of the microneedle array preferably comprises an elongated shaft having two ends, the one end of the shaft forming the base of the microneedle by way of which the microneedle is attached to the planar carrier or by way of which the microneedle is integrated into the planar carrier. The end of the shaft located opposite the base preferably has a tapered shape so as to enable the microneedle to penetrate into the skin as easily as possible. A hollow microneedle can include at least one passage or channel or at least one borehole, which extends from the base of the microneedle to the tip of the microneedle or approximately to the tip of the microneedle. The passages preferably have a round diameter.

The microneedles can be produced from a variety of materials and be made, for example, of a metal, a ceramic material, a semiconductor, an organic material, a polymer or a composite, each in particular having a solid or semi-solid or hollow design.

Preferred materials for producing such microneedles are, for example, pharmaceutically acceptable stainless steel, gold, titanium, nickel, iron, tin, chromium, copper, palladium, platinum, alloys of the aforementioned metals, silicon, silicon dioxide, and polymers. The polymers can particularly preferably include biodegradable polymers, preferably biocompatible polymers and water-soluble polymers, in particular of biological or non-biological origin, preferably polymers such as alpha-hydroxy acids, such as lactic acid and/or glycolic acid, polylactides, polyglycolides, polylactide-co-glycolides, and copolymers with polyethylene glycol, polyanhydrides, poly(ortho)esters, polyurethanes, polybutyric acids, polyvaleric acids, and polylactide-cocaprolactones, polyvinyl pyrrolidone (PVP), glycans, glycosaminoglycans and hyaluronan. The polymers can likewise be non-biodegradable polymers, for example, from the group of the polycarbonates, polyesters or polyacrylamides. In another embodiment, the microneedles are made of a monocrystalline material, such as monocrystalline silicon.

The microneedles can comprise a shaft having a round cross-section or a non-round cross-section, for example having a triangular, quadrangular or polygonal cross-section. The shaft can have one passage or multiple passages, extending from the needle base to the needle tip or approximately to the needle tip. The microneedles can be designed as (barbed) hooks, wherein one or more of these microneedles comprise one or more such hooks. Furthermore, the microneedles can be configured in a helical shape and be rotatably disposed and thereby, when a rotating motion is applied, facilitate the penetration into the skin and effectuate anchoring in the skin (DE 103 53 629 A1), in particular at the desired penetration depth in the epidermis.

The diameter of a microneedle typically ranges between 1 μm and 500 μm, and preferably between 10 μm and 100 μm. The diameter of a passage typically ranges between 3 μm and 80 μm and is suitable for preferably liquid substances, solutions and substance preparations to pass through. The length a microneedle typically ranges between 10 μm, and 1,000 μm, and in particular between 100 μm and 500 μm.

The microneedles are attached at the base thereof to a planar carrier or are integrated into a planar carrier. The microneedles are preferably disposed so as to be situated substantially perpendicularly to the surface area of the carrier. The microneedles can be arranged regularly or irregularly. An arrangement of multiple microneedles can comprise microneedles having differing cross-sectional shapes, differently dimensioned diameters and/or differing lengths.

The arrangement of multiple microneedles can exclusively comprise hollow microneedles. The arrangement can likewise comprise solid microneedles as well as semi-solid composites, such as solid microneedles interspersed with liquid inclusions.

The microneedle array can comprise a planar carrier, wherein the carrier essentially has a disk-shaped, plate-shaped or film-shaped basic shape. The carrier can have a round, an oval, a triangular, a quadrangular or a polygonal base surface area. The carrier can be produced from a variety of materials, such as a metal, a ceramic material, a semiconductor, an organic material, a polymer or a composite. Materials suitable for producing the carrier can preferably be films or web-shaped materials, for example microporous membranes, preferably made of polyethylene (PE) or polypropylene (PP), or diffusion membranes, preferably made of ethylene-vinyl acetate copolymer (EVA) or polyurethane (PUR). Suitable materials for producing the carrier can be selected from the group consisting of polyesters, such as polyethylene terephthalates (PET), polycarbonates (PC), polyether ketones (PAEK), polyethylene naphthalate (PEN), polybutylene terephthalates (PBT), polyurethanes (PU), polystyrenes (PS), polyamides (PA), polyoxymethylene (POM), polyolefins such as polyethylene (PE) and polypropylene (PP), polytetrafluoroethylene (PTFE), polyvinyl chloride (PVC), polyvinylidene chloride (PVDC), polylactate (PLA), and cellulose-based plastic materials, such as cellulose hydrate or cellulose acetate. Suitable materials for producing the carrier can also be selected from the group of metals, which include aluminum, iron, copper, gold, silver, platinum, alloys of the aforementioned metals, and other pharmaceutically acceptable metal foils or metallized films.

The carrier is preferably made of a flexible material, for example a plastic material. A carrier made of a flexible material can better conform to the surface of the skin and the curvature thereof than a carrier made of a non-flexible material. In this way, better contact between the microneedle array and the skin is achieved, thereby improving the reliability of the microneedle array.

It is now essential for the invention that such a microneedle array comprising a color change indicator, and in particular pH indicator, is at least wetted or that preferably a color change indicator, and in particular a pH indicator, is present.

A pH indicator or a corresponding mixture of pH indicators preferably exhibits a color shift or color change visible to the naked eye in the range between pH 4 and 8, and in particular 4.5 to 7. Preferred are pH indicators that, when these rest on the skin, display a significantly different color than when these have penetrated the skin, and in particular reach the stratum corneum as a result of penetration. In this way, it is possible to achieve a clear color change or color difference, which is clearly visible at the latest after the microneedles have been removed.

Suitable pH indicators preferably in the range of pH 4 to 8.5 can be the following, without being limited thereto: nitrazine yellow, bromothymol blue, carminic acid, brazilin, Congo red, neutral red, phenolphthalein, phenolic red, tetrabromophenolphthalein or a mixture thereof.

Likewise, the pH indicators may also be present in the form of mixtures, and corresponding mixed colors can be generated.

In a particularly preferred embodiment, the pH indicator is physiologically acceptable, such as nitrazine yellow and bromothymol blue.

The color change indicator can further be selected from a compound selected from chromoionophores or fluoroionophores, wherein the compound is composed of at least one ionophore covalently bound to at least one molecule, which is selected from the chromophores and fluorophores. The ionophores are molecules capable of complexing ions.

Chromoionophores or fluoroionophores include shape-imparting groups that, in the presence of the intradermal environment (SC, epidermis, dermis), are able to generate a color change, wherein the absorption spectrum of these molecules can be varied by delocalization of the electrons, as a result of which the color of the chromoionophores and/or fluoroionophores changes. The chromoionophores and fluoroionophores are compounds that are composed of one or more ionophoric molecules covalently bound to at least one molecule, which is selected from the chromophores and fluorophores. A chromophore is a compound that absorbs in the visible range, that is, the compound is colored. Within the meaning of the present application, a fluorophore is a compound that absorbs in the UV range and in the visible range, this compound is thus colored.

According to the invention, suitable chromophores or fluorophores are those that are selected from the neutral, acidic or basic nitrated benzene dyes, neutral, acidic or basic (di)azo dyes, including benzidine dyes, quinone dyes, and in particular neutral, acidic or basic anthraquinone dyes, azine dyes, methine dyes, such as neutral, acidic or basic methines and azomethines, triarylmethane dyes, indoamine dyes, natural dyes, such as carotinoids, terpenoids, flavonoids, porphyrins, fluorescein, rhodamine and coumarins, and direct dyes thereof.

A suitable ionophore is, for example, a salt (alkali salt), such as $Na_2$, $K_2HPO_4$, Na, $HHCO_3$, chelating agent, podands, coronands and cryptands, macrocylic compounds, which are referred to as crown ethers or coronands, and macrobicyclic compounds, which are referred to as cryptands. Within the meaning of the present application, "podands" shall be understood to mean molecules having an open structure, which have ion complexing properties and in which the complexation area is a chain containing heteroatoms. These molecules are oligoethers, for example. Within the meaning of the present application, a "coronand" shall be understood to mean two-dimensional molecules having a closed structure, which have ion complexing properties. In general, these are hydrocarbon-based monocyclic molecules that contain heteroatoms. These molecules are, for example, macrocyclic polyethers containing the following unit: —(CH2-CH2-Y)n-, where Y denotes a heteroatom selected from O, S, N and P, and n is an integer greater than 2 and preferably in the range of 4 to 10.

These molecules are, for example, crown ethers, such as 15-crown-5, 18-crown-6; benzocrown ethers, such as benzo-15-crown-5, benzo-18-crown-6, dibenzo-15-crown-5, dibenzo-18-crown-6; monoaza crown ethers or diaza crown ethers, such as aza-15-crown-5, aza-18-crown-6, diaza-15-crown-5, diaza-18-crown-6. Within the meaning of the present invention, "cryptands" shall be understood to mean three-dimensional molecules having a closed structure (cages) that have ion complexing properties. In general, these are hydrocarbon-based bicyclic molecules that contain heteroatoms. These molecules are, for example, macrobicyclic polyethers containing the following unit: —(CH2-CH2-Y)n-, where Y denotes a heteroatom selected from O, S, N and P, and n is an integer greater than 2 and preferably in the range of 2 to 10. The aforementioned color change indicators can likewise contain an oxidizing agent.

The oxidizing agent is preferably selected from hydrogen peroxide, urea peroxide, peracid salts, such as perborates and persulfates, peracids, and particularly preferably from enzymes (oxidases, peroxidases).

In another embodiment, the invention can comprise a color change indicator that detects endogenous enzymes, and in particular peroxidases, which do not form part of the outer layer (epidermis), for example in the case of peroxides due to the body's natural formation of hydrogen peroxide from the oxidation of glucose with the aid of glucose oxidase, such as by means of benzidines, and in particular 3,3',5,5'-tetramethylbenzidine having a specific blue coloration, and phthalazines, such as 5-amino-2,3-dihydrophthalazine-1,4-dione.

Furthermore, ink, and in particular biosensing ink, is a suitable color change indicator.

The color change indicator, and in particular pH indicator, can be integrated or incorporated into the microneedles or into the matrix or formulation of the microarray. Furthermore, the color change indicator can be applied onto the microneedles or onto the carrier. However, it is preferred that the color change indicator, and in particular pH indicator, is an integral part of the microneedle and, for this purpose, can be introduced or incorporated into the microneedles.

In particular, the color change indicator can be added, for example to a polymer, during the production of the microneedles.

A color change indicator, and in particular pH indicator, according to the invention, or a mixture, can be added, for example, during the production of such a microneedle array, for example to the matrix. In another embodiment, such a color change indicator is an integral part or ingredient of a microneedle array or of microneedles, or the microneedles comprise or consist of at least one color change indicator.

In a particularly preferred embodiment, for example, the tip of at least one microneedle is wetted with a color change indicator, or a color change indicator is included in the tip of at least one microneedle. For example, the color change indicator, and in particular pH indicator, can be integrated or incorporated into the tips of the microneedles. In particular, the color change indicator can be added, for example to a polymer, during the production of the tips of the microneedles.

In another preferred embodiment, an active ingredient, and in particular a medicinal drug, can be integrated or incorporated into the microneedles or into the matrix or formulation of the microarray. Furthermore, at least one active ingredient, and in particular a medicinal drug, can be applied onto the microneedles or onto the carrier. However, it is preferred that the active ingredient, and in particular the medicinal drug, is an integral part of the microneedle and, for this purpose, can be introduced or incorporated into the microneedles, and in particular into the tip of the microneedles. In particular, the active ingredient, and in particular the medicinal drug, can be added, for example to a polymer, during the production of the microneedles. The microneedles comprise or consist of at least one medicinal drug.

Such medicinal drugs are preferably those defined in EU Directive 2001/83/EC (Community code relating to medicinal products for human use).

In another specific embodiment, selected microneedles can be provided with a color change indicator, and in particular pH indicator.

This allows the advantageous application of patterns onto the skin, and in particular patterns such as "plus, cross, star, circle" and other arbitrary geometric figures, indicating to the naked eye of the patient or the user the successful application or penetration of the microneedles, also in a visual graphical design.

Moreover, it is preferred that the microneedle array is, or the microneedles are, made entirely or partially of water-soluble or biodegradable polymers (supra), so that a fluid channel is able to release the color change indicators according to the invention more easily.

In another embodiment, the microneedle array is part of a microneedle system. Such a microneedle system can be configured with customary functional objects that allow fixation on the skin as well as easy handling for exerting pressure onto the skin, in particular at least one reservoir and one applicator.

The microneedle system can comprise at least one reservoir, which contains at least one arbitrary substance, and in particular an active ingredient, an auxiliary agent or a medicinal drug, preferably in the form of a solution or preparation.

The reservoir is used to store the at least one arbitrary substance, active ingredient or medicinal drug included in the system.

The reservoir is connected to the passages of the hollow microneedles in such a way that a liquid connection exists between the reservoir and the passages of the microneedles connected to the reservoir. In this way, the content of the reservoir can be released from the reservoir via the passages of the microneedles out of the microneedle system when pressure is exerted onto the reservoir after the microneedle system has been applied to the skin. The preparation on hand exits the microneedle system at or in the vicinity of the tips of the microneedles and can penetrate into the target tissue. The reservoir is usually attached to a surface of the planar carrier, this being the surface of the carrier located opposite the surface of the carrier from which the microneedles project.

The reservoir is easy to compress so as to offer little resistance to the pressure exerted onto the reservoir, and thereby be able to pass the pressure on to the preparation contained in the reservoir for the same to exit. According to one embodiment, the reservoir can be present in the form of a flexible bag, for example.

According to a preferred embodiment, the reservoir is designed as a pad or a balloon and produced from elastic material, for example from an elastomeric polymer or rubber. Examples of polymers include polyesters, such as polyethylene terephthalates (PET), polycarbonates (PC), polyether ketones (PAEK), polyethylene naphthalate (PEN), polybutylene terephthalates (PBT), the polyurethanes (PU), polystyrenes (PS), polyamides (PA), polyoxymethylene (POM), polyolefins such as polyethylene (PE) and polypropylene (PP), polytetrafluoroethylene (PTFE), polyvinyl chloride (PVC), polyvinylidene chloride (PVDC), polylactate (PLA) and cellulose-based plastic materials, such as cellulose hydrate or cellulose acetate.

In another preferred embodiment, the microneedle system comprising a microneedle array is configured with an applicator. Such applicators advantageously allow a pressure mechanism to be activated for the microneedle array to penetrate the skin or stratum corneum (see, for example, WO2008091602A2, WO2016162449A1).

According to a further embodiment, the microneedle array can comprise fixation means that are preferably attached to the skin of a patient or test subject by way of a contact adhesive strip or patch. Suitable contact adhesives include high viscosity substances that adhere to the skin after briefly applying minor pressure, known as pressure-sensitive adhesives (PSA). These have high cohesion and adhesion forces. It is possible, for example, to use poly(meth)acrylate-based, polyisobutylene-based or silicone-based contact adhesives.

The invention thus relates to a microneedle array according to the invention for intradermal delivery, which comprises fixation means for the skin.

According to the invention, the term "intradermal delivery" (synonym: "intracutaneous delivery") describes the administration of arbitrary substances via the microneedle array into the skin and requires the microneedles to pierce the skin.

The invention thus likewise relates to a method for intradermal delivery, wherein at least one substance is delivered by means of a microneedle array comprising fixation means for the skin and a plurality of microneedles on a carrier, wherein the microneedles and/or the carrier include a pH indicator.

The following examples are provided to further describe the invention, without limiting the invention to these examples.

EXAMPLE 1: VERIFICATION OF FUNCTIONALITY

Use of nitrazine yellow (pH indicator) for the delivery by means of microneedles. After successful delivery, a blue coloration is visible to the naked eye after approximately 10 seconds. The different pH value on the skin surface of pH 4 to 5.5 compared to the pH value of the stratum corneum of pH 6.5 to 7 allows a differentiated assessment of the penetration.

a) blue coloration indicates a successful delivery, that is, penetration of the microneedles into the stratum corneum;

b) the skin remains unchanged or takes on a slightly yellowish tint, that is, no successful penetration of the microneedles into the stratum corneum.

In this exemplary embodiment, minute amounts of nitrazine yellow (0.02%) were added as the indicator into the matrix of the microneedles.

EXAMPLE 2

Another exemplary embodiment is the use of color change indicators, which takes advantage of the presence of a substance available in the skin that, in contrast, is not present on the outer layer (epidermis).

Such a color change indicator can be made of one or more substance components. The presence and absence of a substance in the skin are to be understood to represent relative information and, with respect to a successful penetration into the skin, have to reach a distinguishing feature sufficient for the indicator.

Within the meaning of the invention, the use of a glucose-sensitive indicator is, in particular, an obvious choice, without being limited thereto. For this purpose, the reaction known for the detection of glucose in human bodily fluids can be utilized, in which the oxidation of glucose by glucose oxidase, and a subsequent reaction of the reaction products catalyzed by peroxidase, result in the color change of a substance subcomponent of the indicator.

Suitable substances for the differentiated assessment of a color change when the skin has been penetrated are preferably, but not exclusively, 3,3',5,5'-tetramethylbenzidine (TMB/TMBH2) and derivatives derived from the structural class of the benzidines, as well as phthalazines, such as 5-amino-2,3-dihydrophthalazine-1,4-dione, and derivatives derived therefrom.

When using the leuco form of TMB or TMBH2 as the subcomponent of the indicator, the differentiated assessment of the penetration is accordingly made possible by the following:

a) blue coloration indicates a successful delivery, that is, penetration of the microneedles into the stratum corneum; The change in color from TMBH2 (colorless) to TMB (blue) is based on the above-described reaction of the indicator.

b) The skin remaining unchanged means no successful penetration of the microneedles into the stratum corneum and corresponding absence of the reaction of the indicator substances.

The invention claimed is:

1. A microneedle array for use with intradermal delivery, comprising a plurality of microneedles on a carrier, wherein the microneedles comprise at least one color change indicator, the microneedles comprising at least one active ingredient and the microneedles comprising at least one polymer made of biodegradable polymers, biocompatible polymers or water-soluble polymers, a color change or color shift indicating a sufficient penetration depth into the stratum corneum, wherein the color change indicator is an integral part of the microneedles, the at least one color change indicator being introduced or incorporated into the microneedles and wherein the color change indicator is a compound selected from chromoionophores or fluoroionophores, the compound being composed of at least one ionophore covalently bound to at least one molecule, which is selected from chromophores and fluorophores.

2. The microneedle array for use according to claim 1, wherein the color change indicator is added during the production of the microneedles.

3. The microneedle array for use according to claim 2, wherein the microneedles comprise a medicinal drug.

4. The microneedle array for use according to claim 1, wherein the chromophores or fluorophores are selected from the neutral, acidic or basic nitrated benzene dyes, neutral, acidic or basic azo dyes, quinone dyes.

5. The microneedle array according to claim 1, wherein the color change indicator is ink.

6. The microneedle array according to claim 1, wherein the color change indicator detects endogenous enzymes.

7. The microneedle array for use according to claim 1, wherein the color change indicator is included in a tip of the microneedles.

8. The microneedle array for use according to claim 1, wherein the microneedle array comprises fixation means.

9. The microneedle array for use according to claim 1, wherein the microneedle array is accommodated in a microneedle system and comprises at least one reservoir and/or applicator.

10. The microneedle array for use according to claim 1, wherein the chromophores or fluorophores are neutral, acidic or basic methines, azomethines, triarylmethane dyes, indoamine dyes, natural dyes, or direct dyes thereof.

11. The microneedle array according to claim 1, wherein the color change indicator is biosensing ink.

12. The microneedle array according to claim 1, wherein the color change indicator is configured to detect peroxidases, which do not form part of the epidermis, by means of benzidines or phthalazines.

13. A microneedle array for use with intradermal delivery, comprising a plurality of microneedles on a carrier, wherein the microneedles comprise at least one color change indicator which is a biosensing ink, the microneedles comprising at least one active ingredient and the microneedles comprising at least one polymer made of biodegradable polymers, biocompatible polymers or water-soluble polymers, a color change or color shift indicating a sufficient penetration depth into the stratum corneum, wherein the color change indicator is an integral part of the microneedles, the at least one color change indicator being introduced or incorporated into the microneedles.

14. The microneedle array for use according to claim 13, wherein the color change indicator is added during the production of the microneedles.

15. A microneedle array for use with intradermal delivery, comprising a plurality of microneedles on a carrier, wherein the microneedles comprise at least one color change indicator, the microneedles comprising at least one active ingredient and the microneedles comprising at least one polymer made of biodegradable polymers, biocompatible polymers or water-soluble polymers, a color change or color shift indicating a sufficient penetration depth into the stratum corneum, wherein the color change indicator is an integral part of the microneedles, the at least one color change indicator being introduced or incorporated into the microneedles and wherein the color change indicator is configured to detect peroxidases, which do not form part of the epidermis, by means of benzidines or phthalazines.

* * * * *